United States Patent [19]
Wohlstadter

[11] Patent Number: 5,919,681
[45] Date of Patent: *Jul. 6, 1999

[54] METHOD FOR PROMOTING ENZYME DIVERSITY

[76] Inventor: Jacob Wohlstadter, 19 Everett St., #34, Cambridge, Mass. 02138

[ * ] Notice: This patent is subject to a terminal disclaimer.

[21] Appl. No.: 08/505,528

[22] Filed: Jun. 7, 1995

[51] Int. Cl.$^6$ ...................................................... C12N 9/00
[52] U.S. Cl. ......................................... 435/188.5; 435/7.6
[58] Field of Search .................................... 435/7.6, 188.5

[56] References Cited

U.S. PATENT DOCUMENTS

| | | | |
|---|---|---|---|
| 4,792,446 | 12/1988 | Kim et al. | 424/85.8 |
| 4,963,355 | 10/1990 | Kim et al. | 424/85.8 |
| 5,037,750 | 8/1991 | Schochetman et al. | 435/183 |
| 5,156,965 | 10/1992 | Schochetman et al. | 435/188.5 |
| 5,318,897 | 6/1994 | Paul | 435/68.1 |
| 5,401,641 | 3/1995 | Kim et al. | 435/41 |

FOREIGN PATENT DOCUMENTS

| | | |
|---|---|---|
| WO 91/10741 | 7/1991 | WIPO . |
| WO 92/03918 | 3/1992 | WIPO . |
| WO 93/19170 | 9/1993 | WIPO . |
| WO 94/25585 | 11/1994 | WIPO . |
| WO 94/25586 | 11/1994 | WIPO . |

OTHER PUBLICATIONS

Green, N. S., et. al. (1998) BioEssays 20, 227–234.
Oliphant, A. R., et. al. (1989) Proc. Natl. Acad. Sci., USA 86, 9094–9098.
Green, L.L., et. al. (1994) Nature Genetics 7, 13–21.
Lonberg, N., et. al. (1994) Nature 368, 856–859.
Wedemayer, G. J., et. al. (1997) J. Mol. Biol. 268, 390–400.
Sun, M., et. al. (1997) J. Mol. Biol. 271, 374–365.
DeSutter, K, et. al. (1994) Mol. Immun. 31(4), 261–267.
Rosenthal, D., et. al. (1994) Biochem. Biophys. Res. Comm. 202(2), 880–887.

Titmas et al., "Aspects of Antibody–Catalyzed Primary Amide Hydrolysis," *Applied Biochemistry and Biotechnology*, 1994, vol. 47, pp. 277–290.

Suzuki, H. "Recent Advances in Abzyme Studies," *J. Biochem.*, 1994, vol. 115, No. 4, pp. 623–628.

Smiley et al., "Selection of catalytic antibodies for a biosynthetic reaction from a combinatorial cDNA library by complementation of an auxotrophic *Escherichi coli*: Antibodies for orotate decarboxylation," *Proc. Natl. Acad. Sci. USA*, 1994, vol. 91, No. 18, pp. 8319–8323.

Janda, et al., "Direct selection for a catalytic mechanism from combinatorial antibody libraries," *Proc. Natl. Acad. Sci. USA*, 1994, vol. 91, No. 7, pp. 2532–2536.

Taylor, et al., "A transgenic mouse that expresses a diversity of human sequence heavy and light chain immunoglobulins," *Nucleic Acids Research*, 1992, vol. 20, No. 23, 6287–6295.

Sarvetnick, et al., "Increasing the chemical potential of the germ–line antibody repertoire," *Proc. Natl. Acad. Sci. USA*, 1993, vol. 90, No. 9, pp. 4008–4011.

Thorn, et al., "Large rate accelerations in antibody catalysis by strategic use of haptenic charge," *Nature*, 1995, vol. 373, No. 6511, pp. 228–230.

*Primary Examiner*—Charles L. Patterson, Jr.
*Attorney, Agent, or Firm*—Whitman, Breed Abbott & Morgan LLP

[57] ABSTRACT

The invention is directed to a method for generating novel catalysts, particularly high turnover rate enzymes or biocatalysts. Functional catalytic units may be integrated into the germline composition of an animal in order to generate such novel catalysts.

16 Claims, 4 Drawing Sheets

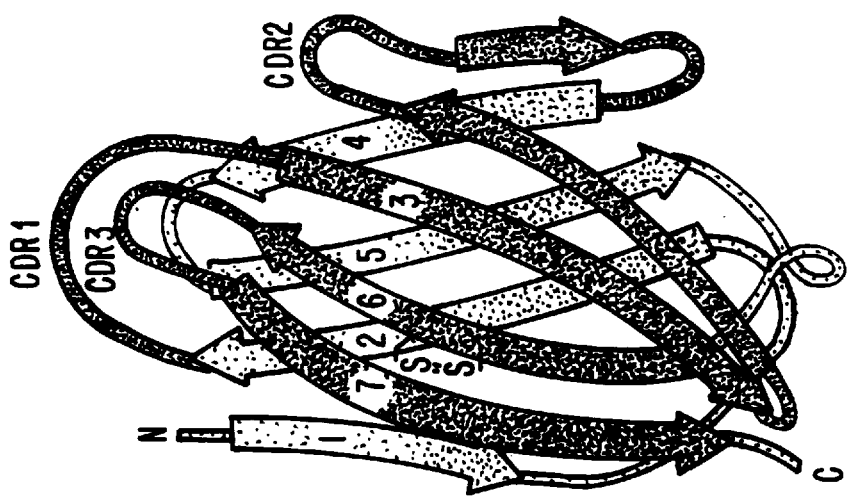
FIG. 2(b) VARIABLE DOMAIN
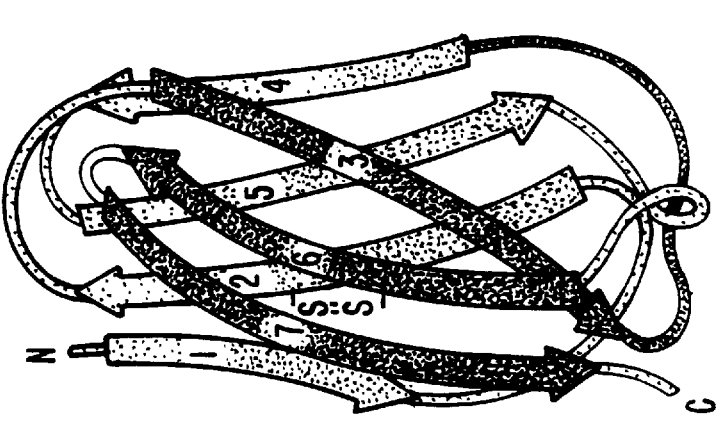
FIG. 2(a) CONSTANT DOMAIN

METHOD FOR PROMOTING ENZYME DIVERSITY

FIELD OF THE INVENTION

The present invention relates broadly to methods for creating novel catalysts, particularly high turnover rate enzymes or biocatalysts, using animals of altered germline sequence. More particularly, the invention relates to methods for promoting rapid evolution or diversification of the specificity regions of an enzyme. The method can be used to produce antibodies with catalytic activity by encoding a functional catalytic unit or a substantial portion thereof into a germline antibody gene locus. And even more particularly, the invention relates to the placement and segmentation of the enzymatic sequences within the antibody gene loci.

BACKGROUND OF THE INVENTION

Over the last decade, research has been devoted to the production of useful antibodies with catalytic activity. Such antibodies are commonly known as catalytic antibodies or Abzymes. Catalytic antibodies with enhanced turnover rates as compared with uncatalyzed reaction rates have been reported by a number of research groups. (see Suzuki et al.,"Recent advances in abzyme studies," 115(4) *Journal Of Biochemistry* 6238(1994) which is incorporated herein by reference, Titmas et al., "Aspects of antibodycatalyzed primary amide hydrolysis, 47(2–3)*Applied Biochemistry & Biotechnology* 277–90(1994) which is incorporated herein by reference). See also U.S. Pat. Nos. 5,037,750 and 5,156,965 to Schochetman and Massey, which are incorporated herein by reference, which teach a method for increasing the rate of chemical reactions involving the conversion of at least one reactant to at least one product.

In some instances, large rate enhancements over uncatalyzed reaction rates have been achieved (see Thorn et al., "Large rate accelerations in antibody catalysis by strategic use of haptenic charge," 373 *Nature* 228–30 (1995) which is incorporated herein by reference). Thus far, however, a generic means has not been found to employ traditional laboratory techniques to produce highly efficient specific catalysis with catalytic antibodies.

The traditional laboratory techniques for producing a catalytic antibody is through the use of transition state analogs (TSA) (see U.S. Pat. No. 4,792,446 to Kim and Kallenbach, which is incorporated herein by reference). The TSA is a stable mimic of the unstable intermediate conformation of a reactant molecule. Animals are immunized with TSA's in the hopes of producing antibodies which by virtue of their ability to bind the TSA's may have the ability to stabilize the transition state of the reactant and to catalyze the formation of the desired product. Hybridomas are then screened by assaying for the desired catalytic activity.

The overwhelming problem that has plagued catalytic antibody development in the vast majority of cases is the lack of high turnover rates. Except in rare instances, catalytic antibodies are orders of magnitude slower catalysts than similar enzymes found in nature.

Recently, however, selection methods have been used to produce catalytic antibodies (see Smiley et al., "Selection of catalytic antibodies for a biosynthetic reaction from a combinatorial cDNA library by complementation of an auxotrophic *Escherichia coli:*antibodies for orotate decarboxylation," 91(18) *Proceedings of the National Academy of Sciences of the United States of America* 8319–23 (1994), which is incorporated herein by reference; Janda et al., "Direct selection for a catalytic mechanism from combinatorial antibody libraries," 91(7) *Proceedings of the National Academy of Sciences of the United States of America* 2532–6), which is incorporated herein by reference. Such methods use selection pressure to isolate antibodies with desired properties instead of the more laborious screening techniques. For example, a catalytic antibody which catalyzes the formation of a cellular growth factor may be selected for in a cell auxotrophic for such growth factor.

Advances in molecular and cell biology have given researchers the ability to alter the germ line genetic constitution of a variety of animals. Pieces of genes, whole genes, and/or chromosomal regions may be selectively deleted or added. Recently these transgenic/knock-out techniques have been used to produce human proteins in other species. In particular, it has been possible to produce human antibodies in rodents (see Green et al., "Antigen-specific human monoclonal antibodies from mice engineered with human Ig heavy and light chain YACs," 7(1) *Nature Genetics* 13–21 (1994), which is incorporated herein by reference; Lonberg et al., "Antigen-specific human antibodies from mice comprising four distinct genetic modifications," 368(6474) *Nature* 856–9 (1994), which is incorporated herein by reference; Taylor et al., "A transgenic mouse that expresses a diversity of human sequence heavy and light chain immunoglobulins," 20–23 *Nucleic Acids Research* 6287–95 (1992), which is incorporated herein by reference). International applications WO 91/10741; WO 94 94/25585; and WO 92/03918 also discuss diversity of human sequence heavy and light chain immunoglobulins and are incorporated herein by reference. The ability to produce human antibodies in rodents allows for the controlled production of therapeutic antibodies of low immunogenicity.

In an extension of the traditional method of the catalytic antibody technique for increasing antibody binding affinity to enzymatically relevant conformations and cofactors, transgenic animals have been utilized to enhance the germline antibody metal ion binding capability. Metal ions are used as co-factors for various enzymes and transgenic mice were produced to more efficiently bind metal cations (see Sarvetnick et al., 1993,"Increasing the chemical potential of the germ-line antibody repertoire," 90(9) *Proceedings of the National Academy of Sciences of the United States of America* 4008–11, which is incorporated herein by reference; WO 94/25586,which is incorporated herein by reference).

In the present invention, rather than promoting binding, as has been done in past studies, applicant proposes integrating functional catalytic units into the germline composition of an animal such that the sequences encoding the specificity determining regions of the enzymatic activity are diversified in an analogous fashion to immunoglobulin variable regions. Such an approach solves the problem of low turnover rate or low catalytic activity.

SUMMARY OF THE INVENTION

Accordingly, the present invention provides a novel method for utilizing transgenic/knock-out germline altering techniques to implant sequences encoding functional catalytic domains and/or structures in the germline antibody sequence of an animal.

In accordance with one aspect of the present invention, such sequences encoding functional catalytic domains and/ or structures are sequences of known enzymes with the desired catalytic function (e.g., hydrolysis of a peptide bond) but with specificity different from the desired catalytic antibody.

In still another aspect of the present invention, the sequences encoding the specificity regions of the implanted functional enzyme are inserted into the germline of the animal so as to correspond to the complementarity determining regions (CDR) of the antibody so as to promote rapid evolution/diversification of the specificity regions of the enzyme. The invention is also in the transgenic implantation of functional catalytic units or enzymes in other (nonantibody) chromosomal regions of high mutation rate (e.g., T cell receptor gene sequences).

And yet another aspect of the present invention, the method provides for a varying array of chimeric antibody/enzyme structures. The placement and segmentation of the enzymatic sequence allows for the production of a multitude of antibody/enzyme structures.

BRIEF DESCRIPTION OF THE DRAWINGS

FIG. 2 illustrates a comparison of the structures of the constant and variable domains of immunoglobulins, β) strands labeled 1–7 have the same topology and similar structures. There are two extra β strands, in the variable domain. The loop between these strands contain the hypervariable region CDR2. The remaining CDR regions are at the same end of the barrel in the loops connecting β strands 2 and 3 and strands 6 and 7. A disulfide bond bridges strand 2 in one sheet with strand 6 in the other sheet in both the constant and the variable domains. (b) The β strands viewed end on, illustrating that one β sheet has the same four βstrands in the two domains.

DETAILED DESCRIPTION OF THE INVENTION

Figure 1:
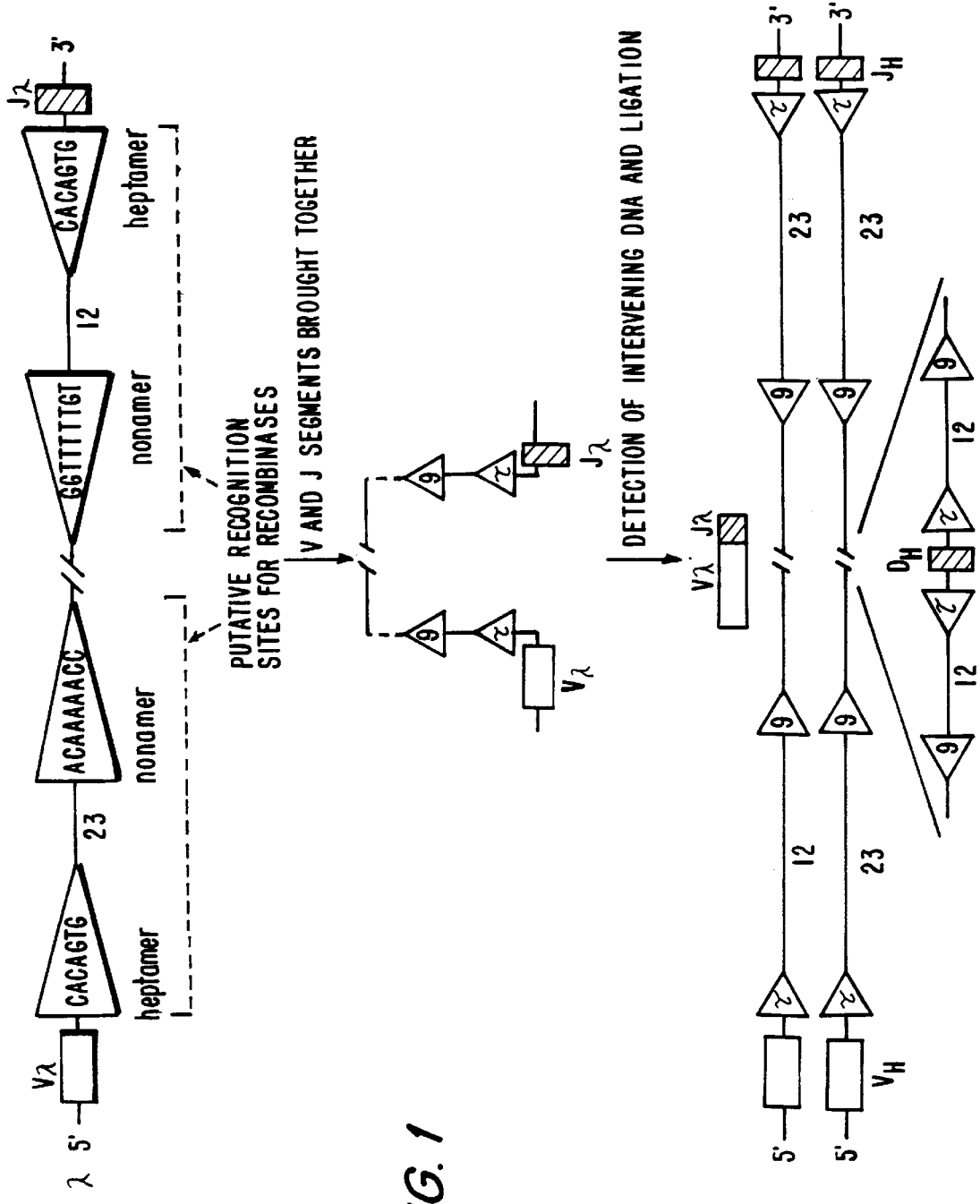
FIG. 1 shows a "DNA recognition sequences for recombinases that mediate Ig gene rearrangement. Conserved heptamer (7bp) and nonamer (9bp) sequences, separated by 12 or 23 base pair spacers, are located adjacent to V and J exons or V, D, and J exons (in the H chain locus). Recombinases presumably recognize these regions and bring the exons together, forming loops of non-coding intervening DNA that are excised and the exons are joined. Alternatively, the exons can be joined by a process of inversion, followed by excision and ligation." 302 *Nature* 575(1983).
Figure 3A:
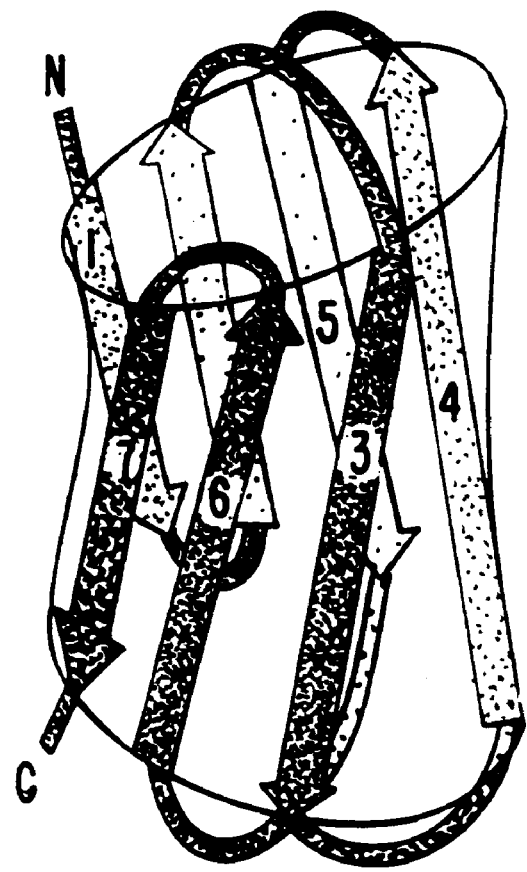
FIG. 3 is a view of the constant domains of immunoglobulins folded into a compressed antiparallel β barrel built up from one three-stranded β sheet packed against a four-stranded sheet (a). The topological diagrams (b) show the connected Greek key motifs of this fold.
Figure 3B:
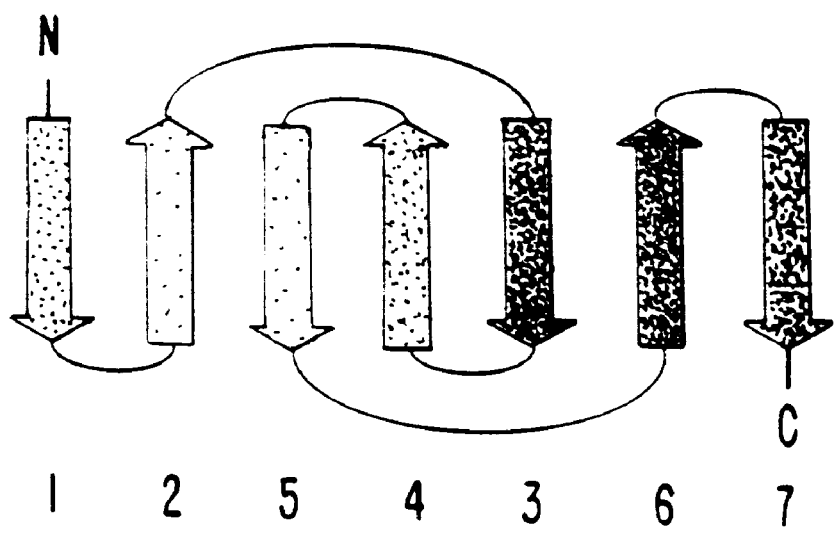
Figure 4A:
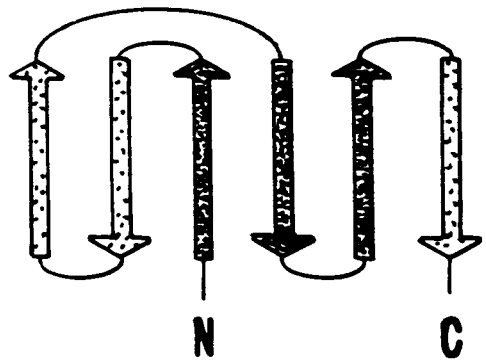
FIG. 4 is a topology diagram of the domain structure of chymotrypsin. The chain is folded into a Greek key motiff followed by a hairpin motif that are arranged as a six-stranded antiparallel β barrel.
Figure 4B:
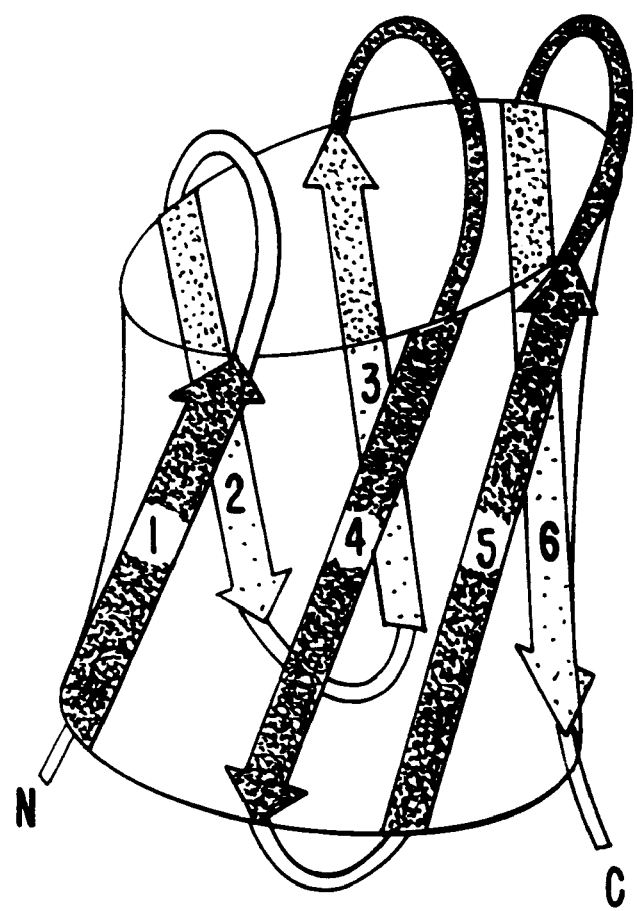

The following definitions are necessary for a proper understanding of the invention:

A catalytic engine is a functional catalytic unit capable of altering the rate of a reaction.

An evolutionary starting point is defined as a sequence (or protein encoded by said sequence) which encodes or has a desired property or is closely related to a sequence or protein with such property (e.g., catalytic activity).

As disclosed in WO 93/19170 to Wohlstadter, which is incorporated herein by reference, evolutionary starting points may be utilized to produce high turnover rate enzymes and/or other biocatalysts (e.g. ribozymes). In a broad sense enzymes and/or other biocatalysts may be considered to have two functionalities: the catalytic center which drives catalysis (catalytic engine) and the surrounding specificity regions which determine the substrate or reactant selectivity of the enzyme. Empirically, it has been found that functional catalytic domains or catalytic engines are common to enzymes of different specificity (see Branden et al., "Introduction to Protein Structure," Garland Publishing (1991), which is incorporated herein by reference). This empirical data suggests that it is more efficient to maintain a functional catalytic domain or catalytic engine and evolve the specificity domains to create enzymes for new substrates than to evolve different catalytic functional units. Efficient biocatalysts require precise structural orientation of specific chemical moieties and often require complex serial temporal and spatial interaction with the reactant substrate (see Walsh, "Enzymatic Reaction Mechanisms," Freeman and Co., (1979), which is incorporated herein by reference). Simply binding to a specific molecular structure may be carried out with a variety of different molecules. This is best exemplified by antibodies. Many, substantially different antibody sequence/structures are capable of high affinity binding to the same antigen epitope. Further emperical evidence suggests that the stringent complex requirements needed to create a functional catalytic unit drastically restricts the number of chemical/structural conformations which are capable of carrying out catalysis whereas many different chemical/structural conformations may confer substantially similar binding affinity. For example, different proteins evolve substantially similar functional catalytic mechanisms. Even though such enzymes primary amino acid sequence are unrelated they convergently evolve the same catalytic mechanism (see Branden). The evolutionary data indicates that to create a biocatalyst of new specificity it is evolutionarily more efficient to utilize an existing functional catalytic unit and evolve the specificity determining regions to achieve the desired substrate selectivity since only a relatively more restricted set of chemical/structural conformations are capable of forming a high efficiency catalytic unit. The current invention is in the increased efficiency of creating antibodies with catalytic activity by altering the germline antibody sequence of an animal to encode a functional catalytic unit or substantially all of a functional catalytic unit or enzyme.

A variety of different transition state analogs have been synthesized and used to immunize laboratory animals. TSA's and other immunogens of varying structure and charge have been utilized to elicit antibodies with catalytic activity with varying shape complementary structures and charge complimentary structures (for example, see Suzuki; Thorn; U.S. Pat. Nos. 4,792,446; 4,963,355; 5,156,965; 5,401,641; 5,318,897; which are incorporated herein by reference). TSA's may also be produced with extended structures to more fully mimic the structure of the desired substrate to increase selectivity. Additionally, immunization may be carried out using suicide substrate inhibitors (substrates which covalently bind to functional catalytic domains). A variety of antigens may be utilized in the present invention. Depending on the desired degree of selectivity, antigens of more exact and/or extensive similarity to the desired substrate may be used. In some instances substantially all of a substrate may be utilized with only minor alterations or in other cases the substrate itself may be utilized. In a preferred embodiment of the invention enzyme inhibitors and or suicide substrates are used as antigens or components of antigens. In a particularly preferred embodiment of the invention enzyme inhibitors and or suicide substrates are integrated into the substrate or an analog therof at the desired site of catalytic action on the substrate.

In the last several years advances in transgenic/knockout germline alteration have allowed the production of animals with varied properties. A variety of different groups have been able to alter the germline of antibody genes so as to produce human antibodies in other species. As is known by one skilled in the art, new genes and/or sequences may be introduced into an animal's germline and/or endogenous genes and/or sequences may be inactivated, disrupted, and/or deleted. In the current invention, such germline altering techniques are utilized to insert a functional enzyme sequence so as to create a chimeric antibody enzyme molecule such that the enzyme portion of the chimeric protein undergoes immunological evolution and selection generating antibodies with desired enzymatic activity. In a preferred embodiment of the invention both the antibody sequences and the enzyme sequences are human sequences so as to limit the potential immunogenicity of the resulting catalytic antibody. In one embodiment, the use of yeast artificial chromosones can be employed.

Antibodies are composed of several immunoglobulin domains which are covalently attached into the commonly known 'Y shaped' structure of two heavy chains and two light chains. Each heavy chain and each light chain contain one variable immunoglobulin domain and the remaining immunoglobulin domains are constant domains. Although slightly different in structure both variable and constant domains have antiparallel β barrel tertiary structures (see FIG.2). The loops connecting beta strands in the variable domains termed CDR1, CDR2 and CDR3 (Complimentary Determining Regions 1, 2 and 3) are found to vary widely between antibodies and confer antibody specificity. Antibody diversity is generated by a variety of means. For example, diversity may be generated by (1) multiple different germline genes (2) combinatorial diversity (3) junctional diversity including (a) imprecise DNA rearrangement and (b) N region diversification (4) varying combinations of heavy and light chain proteins and (5) somatic mutation (see Abbas et al., "Cellular and Molecular Immunology Second Edition," Saunders Co., (1994); Paul, "Fundamental Immunology Third Edition," Raven Press (1993), which is incorporated herein by reference). Through proper insertion of the enzyme or functional catalytic unit within the germline such diversification mechanisms are imposed on the enzymatic portion of the antibody enzyme protein. For example, the V, D, and J regions of an antibody may be replaced with sequences from a known human enzyme. The intronic configuration of the antibody gene locus is maintained to foster extensive diversification. For example, repetitive sequences (nanomer and octamer) as well as intronic spacing is maintained (see FIG. 2).

The invention is also in the placement and segmentation of the enzymatic sequence. For example, those domains of the inserted enzyme sequence which are spatially located in or around the active site and or those residues which may play a role in extensive specific substrate binding are placed in those regions which are capable of the highest diversification (e.g. the CDR regions). For example, chymotrypsin also folds in an antiparallel beta barrel like an immunoglobulin domain (see FIG. 3). The active site and substrate specificity regions are located in the protein sequence bridging beta strands of the beta barrel as are the CDR regions in an immunoglobulin variable region.

The invention is also in a varying array of chimeric antibody/enzyme structures. In one embodiment the enzymatic sequence replaces one or multiple variable domains. Further multiple different enzymatic sequences may be integrated into the germline in an analogous fashion to the multiple V, D and J variable regions to create an extensively altered germline and to further increase diversification. In another embodiment the enzymatic sequence with inserted variable region intronic spacing and signal sequences may be inserted into the germline so as to incorporate the enzymatic domain as an amino terminal fusion. In another embodiment such amino terminal enzymatic fusions may have antibody variable regions replaced with constant immunoglobulin regions thereby limiting diversification to only the enzymatic region. In another embodiment of the invention sequences encoding enzymatic functionality are inserted into the germline antibody locus such that the enzyme sequence is subject to immunoglobulin variable region diversification, but is not covalently linked to an immunoglobulin domain. A wide variety of such different structures may be utilized and employed in the invention by one skilled in the art.

The invention is also in the method and sequence of production of catalytic antibodies using the altered germline animals of the invention. For example, immunization with a variety of different TSA types, inhibitors, and/or suicide substrates (see Suzuki; Thorn; U.S. Pat. Nos. 4,792,446; 4,963,355; 5,156,965; 5,401,641, which are incorporated herein by reference) may be carried out in a sequential fashion to elicit antibodies with increasing affinity. In another embodiment after immunization of the animals of the invention a resulting enzymatic antibody sequence is then transgenically integrated into the germline sequence of another animal. For example, this technique can be useful in the step-wise iterative evolution of a catalytic antibody. In this way evolutionary progress may be continued at a germline level.

The immune system selects antibodies based on binding affinity and/or binding kinetics. An enzyme with high turnover rates is required to bind the reactant, catalyze the formation of the product and release the product to allow access of another reactant to the functional active site of the enzyme. Whereas a high turnover rate enzyme requires the release of the product an antibody is selected for high binding affinity. In another embodiment of the invention the transgenically inserted enzymatic or catalytic functional unit is selectively altered with a relatively small set of mutations so as to substantially lower the catalytic activity (e.g., mutation of the catalytic triad residues of a serine protease). In this way the substrate of interest may be used as an antigen and selectivity for the desired substrate may be achieved. After selection for binding/selectivity the small set of mutations are reverted (e.g., through specific mutation, in vitro screening, selection, etc.) in order to increase the catalytic turnover. The resulting catalytic antibody may be further selected using enzymatic inhibitor, suicide substrates and/or TSA's.

The invention is in the iterative immunization of the altered germline animals of the invention and also in the simultaneous immunization with multiple antigens. Iterative immunization may use the same antigen or different antigens to tailor the progression of the immune response. Multiple antigens may be delivered simultaneously to bias the immune response as desired. Many techniques are available to one skilled in the art to optimize optimize antibody production. For example, adjuvants may be employed to heighten an immune response.

The antibodies with enzymatic activity of the current invention may be modified through techniques known in the art. For example, three dimensional structural information may be used for rational design modifications of the catalytic antibodies. In a further example, in vitro mutagenesis and screening and or selection may be employed to further develop the enzymatic antibodies of the current invention.

One skilled in the art would realize that a wide variety of species may be utilized to generate catalytic antibodies. For example, mice, rats, rabbits, goats, sheep, cows etc. as well as non-mammalian species may be used. Further one skilled in the art would realize that a wide variety of enzymatic functionalities and enzyme families as well as specific enzymes may be utilized in the invention (U.S. Pat. Nos. 4,792,446; 4,963,355; 5,156,965; 5,401,641; 5,229,272; 5,194,585; 5,236,836, which are incorporated herein by reference).

One skilled in the art would realize that various combinations of the above-identified techniques may be employed to practice the claimed invention.

I claim:

1. A method for generating biocatalysts by in vivo selection for catalytic antibodies having modified binding properties which comprises:
   (a) selecting a sequence encoding a functional catalytic domain of an enzyme;
   (b) inserting said sequence encoding the functional catalytic domain into the antibody gene locus of an animal;
   (c) harvesting putative biocatalysts generated by said animal; and
   (d) identifying those of the generated putative antibodies having the desired enzymatic activity.

2. The method according to claim 1, wherein said sequence encoding the functional catalytic domain and the antibody are of human origin.

3. The method according to claim 1, wherein the endogenous antibody production of the animal is eliminated.

4. The method according to claim 1, wherein the animal is a mouse.

5. A method for generating biocatalysts by in vivo selection for catalytic antibodies having modified binding properties which comprises:
   (a) selecting a sequence encoding a functional catalytic domain of an enzyme;
   (b) inserting said sequence encoding the functional catalytic domain into the antibody gene locus of an animal;
   (c) immunizing said animal with an immunogen;
   (d) harvesting putative biocatalysts generated by said animal; and
   (e) identifying the generated putative antibodies with desired enzymatic activity.

6. The method according to claim 5, wherein said sequence encoding the functional catalytic domain and the antibody are of human origin.

7. The method according to claim 5, wherein the endogenous antibody production of the animal is eliminated.

8. The method according to claim 5, wherein the animal is a mouse.

9. A method for generating chimeric antibody/enzyme fusion molecules by in vivo selection which comprises:
   (a) selecting a sequence encoding a functional catalytic domain of an enzyme;
   (b) inserting said sequence encoding the functional catalytic domain into the antibody gene locus of an animal, such that said sequence encoding the functional catalytic domain may undergo immunoglobulin variable region diversification;
   (c) harvesting putative chimeric antibody/enzyme fusion biocatalysts generated by said animal; and
   (d) identifying the generated putative chimeric antibody/enzyme fusion molecules having the desired enzymatic activity.

10. The method according to claim 9, wherein said sequence encoding the functional catalytic domain and said generated chimeric antibody/enzyme fusion biocatalyst are of human origin.

11. The method according to claim 9, wherein the endogenous antibody production of the animal is eliminated.

12. The method according to claim 9, wherein the animal is a mouse.

13. A method for generating chimeric antibody/enzyme fusion biocatalysts by in vivo selection which comprises:
   (a) selecting a sequence encoding a functional catalytic domain of an enzyme;
   (b) inserting said sequence encoding the functional catalytic domain into the antibody gene locus of an animal, such that said sequence encoding the functional catalytic domain may undergo immunoglobulin variable region diversification;
   (c) immunizing an animal containing said antibody gene locus or a progeny thereof having said gene locus;
   (d) harvesting putative chimeric antibody/enzyme fusion biocatalysts generated by said animal; and
   (e) selecting the generated putative chimeric antibody/enzyme fusion biocatalysts having the desired enzymatic activity.

14. The method according to claim 13, wherein said sequence encoding the functional catalytic domain and said generated chimeric antibody/enzyme fusion biocatalyst are of human origin.

15. The method according to claim 13, wherein the endogenous antibody production of the animal is eliminated.

16. The method according to claim 13, wherein the animal is a mouse.

* * * * *